(12) United States Patent
Derrer et al.

(10) Patent No.: US 7,718,828 B2
(45) Date of Patent: May 18, 2010

(54) PROCESS FOR PRODUCING 2,2,3-TRIMETHYLCYCLOPENT-3-ENECARBALDEHYDE (CAMPHOLYTIC ALDEHYDE)

(75) Inventors: Samuel Derrer, Fällanden (CH); Urs Mueller, Duebendorf (CH)

(73) Assignee: Givandan SA, Vernier (CH)

( * ) Notice: Subject to any disclaimer, the term of this patent is extended or adjusted under 35 U.S.C. 154(b) by 0 days.

(21) Appl. No.: 12/376,035

(22) PCT Filed: Aug. 7, 2007

(86) PCT No.: PCT/CH2007/000385

§ 371 (c)(1),
(2), (4) Date: Mar. 24, 2009

(87) PCT Pub. No.: WO2008/017184

PCT Pub. Date: Feb. 14, 2008

(65) Prior Publication Data

US 2010/0004489 A1    Jan. 7, 2010

(30) Foreign Application Priority Data

Aug. 11, 2006    (EP)    ................................. 06016773

(51) Int. Cl.
*C07C 45/62*    (2006.01)
(52) U.S. Cl. ...................................................... 568/446
(58) Field of Classification Search .................. 568/446
See application file for complete search history.

(56) References Cited

OTHER PUBLICATIONS

Amri, H. et al: "reaction of Trimethylamine Dihydroflouride with Simple Epoxides and .alpha.-functional Derivatives of a Bicyclo[3.1.1]Heptane Monoterpene" (Including English Language Abstract).

Bessiere-Chretien, Yvonne et al "Epoxyverbanone" Comptes Rendus Des Seances de L'Academie des Dciences, Serie C: Sciences Chimiques, vol. 273, No. 3 ,1971, pp. 272-275 (Including English Language Abstract).

*Primary Examiner*—Sikarl A Witherspoon
(74) *Attorney, Agent, or Firm*—Norris McLaughlin & Marcus, PA

(57) ABSTRACT

A method for the production of campholytic aldehyde starting from campholenic aldehyde in the presence of a copper catalyst and a solvent.

8 Claims, No Drawings

PROCESS FOR PRODUCING 2,2,3-TRIMETHYLCYCLOPENT-3-ENECARBALDEHYDE (CAMPHOLYTIC ALDEHYDE)

This is an application filed under 35 USC 371 of PCT/CH2007/000385.

Disclosed is a method of producing 2,2,3-trimethyl-3-cyclopentene-1-carboxaldehyde, also known as campholytic aldehyde.

Up to now, campholytic aldehyde has been prepared from expensive epoxy-verbenone as described e.g. by Bessiere-Chretien et al., Comptes Rendus des Seances de l'Academie des Sciences, Serie C: Sciences Chimiques (1971), 273(3), page 272-275, or Amri et al., Journal de la Societe Chimique de Tunisie (1983), 10, page 25-32.

The inventors have now found a new process for the production of campholytic aldehyde in high yields starting from campholenic aldehyde (2-(2,2,3-trimethylcyclopent-3-enyl) acetaldehyde), which is a relatively cheap bulk chemical, resulting in a relatively cheap campholytic aldehyde, which in turn may be used for the production of a new class of molecules. For example, it could be used for the production of a plurality of new fragrance ingredients. Furthermore, by using a relatively cheap starting material, the overall costs of production of certain fragrance ingredients can be held down.

The invention therefore provides a process for the preparation of campholytic aldehyde comprising A) reacting campholenic aldehyde with an amine of formula (I)

wherein $R^1$ and $R^2$ are independently selected from $C_1$-$C_6$ alkyl or benzyl; or $R^1$ and $R^2$ forming together with the nitrogen atom to which they are attached a cycling ring containing 4 to 7 carbon atoms and none or one further hetero atom selected from nitrogen and oxygen, e.g. morpholine, pyrrolidine, and piperidine;

B) treating the resulting product of A) with oxygen to prepare campholytic aldehyde in the presence of a copper catalyst and a solvent, with the proviso that the solvent is not a chlorinated solvent.

As used in relation to the compounds of formula (I) "alkyl" unless otherwise indicated refers to linear or branched alkyl, saturated or unsaturated alkyl and cycloalkyl, such as methyl, ethyl, butyl, hexyl, and cyclohexyl.

According to the present invention, campholenic aldehyde is converted into the corresponding enamine, if necessary under Dean-Stark conditions known to the person skilled in the art. This is then oxidatively degraded using oxygen or air and copper catalysis to the corresponding campholytic aldehyde. The last step is performed in the presence of a solvent which is necessary for the reaction to proceed. A critical parameter for the selection of the solvent is the stability of the starting enamine. Thus, protic solvents are usually not ideal. Also, it is necessary that at least a small part of the copper catalyst be soluble in the solvent. The solvent may be selected from the family of secondary amides, such as dimethyl formamide or N-methyl-pyrrolidone and the like, and from the family of nitrites, such as acetonitrile, propionitrile and butyronitrile. It may also be an ether such as methyl tert.-butyl ether, tetrahydrofuran, 1,3-dioxane, 1,2-dimethoxyethane, diglyme and the like. However, although chlorinated solvents have the ability to dissolve certain copper catalysts, very little or no transformation was observed in the presence of chlorinated solvents. Particularly preferred are polar aprotic solvents such as acetonitrile, dimethyl formamide and N-methyl-pyrrolidone.

Any copper(I) or copper(II) compound can be used to catalyse this reaction. A list of such salts is given hereinunder by way of example but not limiting the choice.

Copper(I) compounds, such as copper(I) acetate, copper(I) bromide, copper(I) chloride, copper(I) iodide, copper(I) fluoride, copper(I) cyanide, copper(I) oxide, copper(I) thiocyanide, and complex compounds, such as tetrakis(acetonitrile) copper(I) hexafluorophosphate.

Copper(II) compounds, such as copper(II) acetate, copper(II) acetylacetonate, copper(II) bromide, copper(II) chloride, copper(II) ethylacetoacetate, copper(II) fluoride, copper(II) oxide, copper(II) nitrate, copper(II) oxalate, copper(II) perchlorate, copper(II) phthalocyanine, copper(II) sulfate, copper(II) tartrate, copper(II) tetrafluoroborate, copper(II) hydroxide, copper(II) D-gluconate and copper(II) formate.

The preferred catalysts are copper(I) chloride and copper(II) chloride.

The reaction temperature depends on the solvent used and can be between the solidifying and boiling temperature of the reaction mixture. Preferred reaction temperatures are from 0° C. to 50° C. and the most preferred temperature is about 20 to about 30° C.

Although air (natural or synthetic: 20% oxygen 80% nitrogen) suffices to effect the desired reaction, neat oxygen gas is preferred and most efficient. However, any oxygen-nitrogen mixture can in principle be used.

Amines of formula (I) include but are not limited to dimethylamine, diethylamine, dibutylamine, dihexylamine, dicyclohexylamine, N-methyl-benzylamine, morpholine, pyrolidine and piperidine.

Following the general process as herein above described substantially no racemization of the chiral center of champholenic aldehyde was observed. For example, starting from (S)-(+) campholenic aldehyde at about 30% ee results in (R)-(−) campholytic aldehyde at about 27% ee, and starting from (R)-(−) campholenic aldehyde at about 80% ee results in (S)-(+) campholytic aldehyde at about 81% ee.

The invention is now further described with reference to the following non-limiting examples. These examples are for the purpose of illustration only and it is understood that variations and modifications can be made by one skilled in the art.

EXAMPLE

A) 4-((1E)-2-(2,2,3-trimethylcyclopent-3-enyl)vinyl) morpholine

Procedure A

A mixture of campholenic aldehyde (138 g, 0.9 mol) and morpholine (95.7 g, 1.1 mol) is dissolved in cyclohexane (400 ml) and a catalytic amount of p-toluene sulfonic acid (1 g) is added. The mixture is heated to reflux with stirring. Under Dean-Stark conditions, approx. 18 g of water is collected within 3 h. Upon cooling to room temperature, the mixture is washed with water (200 ml), dried over sodium sulfate and concentrated in vacuo to furnish the crude morpholine enamine (235 g). This is purified by distillation over a 5 cm- Vigreux column at reduced pressure to afford the title compound (186 g) as a pale yellow oil, bp. 110° C. (0.1 mbar).

$^1$H-NMR: δ 5.80 (1H, d, J=13.8, =CHN), 5.25-5.23 (1H, m, =CH), 4.48 (1H, dd, J=13.8, 9.2, =CH), 3.73 (4H, apparent t, J=4.9, 2×OCH$_2$), 2.80 (4H, apparent t, J=4.9, 2×NCH$_2$), 2.27-2.21 (2H, m, CH and CHH), 2.08-1.97 (1H, m, CHH), 1.62-1.60 (3H, m, Me), 0.92 (3H, s, Me), and 0.74 (3H, s, Me).

$^{13}$C-NMR: δ 148.3 (s), 139.8 (d), 121.6 (d), 103.2 (d), 66.5 (t), 52.6 (d), 49.6 (t), 47.7 (s), 36.9 (t), 25.1 (q), 20.2 (q), and 12.9 (q).

MS: 221 (M$^+$, 100), 206(93), 178(13), 139(33), 126(25), 119(32), 113(29), 91(24), 79(16), 67(14), 55(16), 41(24).

Procedure B

A flask is charged with campholenic aldehyde (1200 g, 6.9 mol) and morpholine (600 g, 6.9 mol) is added under stirring. The mixture is exothermic and warms to 75° C., while water separates. The mixture is transferred into a separating funnel and the water (105 ml) is removed. The crude product is distilled through a 10 cm-Vigruex column to afford the desired product (1240 g) as a pale yellow oil, bp. 118-120° C. (0.2 mbar).

B) Campholytic aldehyde
(2,2,3-trimethylcyclopent-3-enecarbaldehyde)

4-((1E)-2-(2,2,3-trimethylcyclopent-3-enyl)vinyl)morpholine (45 g, 0.2 mol) is dissolved in a solvent (see table below, 200 ml) and a copper catalyst (see table below, 0.01 mol) is added. Then, a stream of oxygen (or air, see table below) is bubbled through the solution for 3.5 h at 25-30° C. and under vigorous stirring, after which the starting morpholine enamine is fully consumed. The mixture is poured into ice/water (500 ml) and extracted with hexane or pentane (3×250 ml). The combined organic phases are washed with ammonium chloride solution (aq., sat., 250 ml), dried over sodium sulfate and concentrated in vacuo to give the crude product as a yellowish to greenish liquid. This is distilled under reduced pressure through a 6 cm-Widmer column to afford the required campholytic aldehyde as a very pale yellow oil, boiling point 67-68° C. (~15 mbar).

$^1$H-NMR: δ 9.76 (1H, d, J=3.2, CHO), 5.26-5.24 (1H, m, =CH), 2.69-2.65 (1H, m, CH), 2.63-2.55 (1H, m, CHH), 2.41-2.31 (1H, m, CHH), 1.63-1.60 (3H, m, Me), 1.21 (3H, s, Me), and 1.00 (3H, s, Me).

$^{13}$C-NMR: δ 204.5 (d), 146.8 (s), 121.0 (d), 61.5 (d), 48.9 (s), 29.3 (t), 25.6 (q), 21.6 (q), and 11.7 (q).

MS: 138(M$^+$, 26), 123(58), 109(22), 95(100), 79(20), 67(48), 55(28), 41(23).

When starting with from (R)-campholenic aldehyde (~80% ee), the optical rotation is: [α]$_D^{22}$=+9.8° (5.09 in EtOH).

When starting with from (S)-campholenic aldehyde (~30% ee), the optical rotation is: [α]$_D^{22}$=−3.8° (5.01 in EtOH).

| Solvent | Catalyst | Oxygen | Product | Remarks |
|---|---|---|---|---|
| Acetontrile | CuCl | 100% | 22.5 g | clean reaction |
| Acetontrile | CuCl$_2$*2H$_2$O | 100% | 20.2 g | clean reaction |
| Acetontrile | CuCl | 20% (air) | not isolated | very slow reaction |
| Dimethylformamide | CuCl | 100% | 22.4 g | clean reaction |
| N-Methylpyrrolidone | CuCl | 100% | 21.6 g | clean reaction |
| Methyl tert-butyl ether | CuCl | 100% | 6.5 g | sluggish reaction* |
| Chloroform | CuCl | 100% | — | no reaction |
| Methylene chloride | CuCl | 100% | — | no reaction |
| No solvent | CuCl | 100% | — | no reaction |

*1.2 g of clean 2,2,3-trimethyl-3-cyclopenten-1-one was isolated as by-product

The invention claimed is:

1. A process for the preparation of campholytic aldehyde comprising:
    (a) reacting campholenic aldehyde with an amine of formula (I)

(I)

wherein
    R$^1$ and R$^2$ are independently selected from C$_1$-C$_6$ alkyl or benzyl; or
    R$^1$ and R$^2$ forming together with the nitrogen atom to which they are attached a cycling ring containing 4 to 7 carbon atoms and none or one further hetero atom selected from nitrogen and oxygen;
    (b) treating the resulting product of step 1 with oxygen to prepare campholytic aldehyde in the presence of a copper catalyst and a solvent, with the proviso that the solvent is not a chlorinated solvent.

2. A process according to claim 1 wherein the amine of formula (I) is morpholine.

3. A process according to claim 1 wherein the solvent is a polar aprotic solvent.

4. A process according to claim 1 wherein the solvent is selected from acetonitrile, dimethyl formamide and N-methyl-pyrrolidone.

5. A process according to claim 1 wherein the copper catalyst is selected from the group consisting of copper (I) chloride and copper (II) chloride.

6. A process according to claim 2 wherein the solvent is a polar aprotic solvent.

7. A process according to claim 2 wherein the solvent is selected from from acetonitrile, dimethyl formamide and N-methyl-pyrrolidone.

8. A process according to claim 2 wherein the copper catalyst is selected from the group consisting of copper (I) chloride and copper (II) chloride.

* * * * *